United States Patent [19]

Hamelin

[11] Patent Number: 5,792,611

[45] Date of Patent: Aug. 11, 1998

[54] DETECTION OF PLANT PATHOGENIC FUNGI

[75] Inventor: Richard C. Hamelin, St-Augustine-de-Desmaures, Canada

[73] Assignee: Natural Resources Canada, Canadian Forest Service, Ste-Foy, Canada

[21] Appl. No.: 652,127

[22] Filed: May 23, 1996

[51] Int. Cl.$^6$ .................................................. C12Q 1/68
[52] U.S. Cl. ................. 435/6; 435/4; 536/24.32; 536/24.33; 935/8; 935/77; 935/78
[58] Field of Search .................. 435/6, 4; 536/24.32, 536/24.33; 935/8, 77, 78

[56] References Cited

U.S. PATENT DOCUMENTS 5,324,632  6/1994  Weisburg et al. .......................... 435/6
5,434,048  7/1995  Simon et al. ............................... 435/6

FOREIGN PATENT DOCUMENTS

WO 95/29260  11/1995  WIPO.

OTHER PUBLICATIONS

Brown et al. (1993) FEMS Microbiology Letters. vol. 108, pp. 117–120.

Accession No. U36443, Dumas, M. et al. (17 Oct. 1995) EMBL/GenBank/DDBJ Database. Cylindrocladium Floridanum rDNA internal transcribed spacer.

*Primary Examiner*—Dian C. Jacobson
*Assistant Examiner*—Enrique D. Longton
*Attorney, Agent, or Firm*—George A. Seaby

[57] ABSTRACT

Root rots are serious conifer nursery diseases. At present, seedlings are inspected visually to determine whether they show symptoms of disease. *Cylindrocarpon destructans* and *Cylindrocarpon floridanum* are two important causal agents of root rots. A substantially more efficient and reliable method of detecting the presence of these fungi directly from infected tissue involves the use of a set of DNA primers which can be used in conjunction with the polymerase chain reaction (PCR) to create species specific probes for detecting species of each fungi.

4 Claims, 5 Drawing Sheets

FIG. 1

|       | 5          | 15         | 25         | 35         | 45         |
|-------|------------|------------|------------|------------|------------|
| FLOR  | CTTGGTCATT | TAGAGGAAGT | AAAAGTCGTA | ACAAGGTCTC | CGTTGGTGAA |
| DESTA | .......... | .......... | .......... | .......... | .......... |
| DESTB | .......... | .......... | .......... | .......... | .......... |
| DESTC | .......... | .......... | .......... | .......... | .......... |

|       | 55         | 65         | 75         | 85         | 95         |
|-------|------------|------------|------------|------------|------------|
| FLOR  | CCAGCGGAGG | GATCATTACC | GAGTTTACAA | CTCCCAAACC | CCATGTGAAC |
| DESTA | .......... | .......... | .......... | .......... | .......... |
| DESTB | .......... | .......... | .......... | .......... | .......... |
| DESTC | .......... | .......... | .......... | .......... | .......... |

|       | 105        | 115        | 125        | 135        | 145        |
|-------|------------|------------|------------|------------|------------|
| FLOR  | ATACCTGTTT | CGTTCCCCTCG | GCGGTGTCCG | G--CAACGGC | CCGCCAGAGG |
| DESTA | .A........ | ...G...... | .....C.T.. | CTT.GG.A.. | .......... |
| DESTB | .A........ | ...G...... | .....C.T.. | CTT.GG.A.. | .......... |
| DESTC | .TA....... | ...G...... | .....C.T.. | TTC.GA.A.. | .......... |

|       | 155        | 165        | 175        | 185        | 195        |
|-------|------------|------------|------------|------------|------------|
| FLOR  | ACCCAACAAA | CTCTTTTGAA | TTTTTCAGTA | TCTTCTGAGT | AAAA-AAAAC |
| DESTA | ....A..CC. | .TTGA..TT. | .ACAGT.--- | .......... | ...T-G.TTA |
| DESTB | ....A..CC. | .TTGA..TT. | .ACAGT.--- | .......... | ...T-G.TTA |
| DESTC | ....C..AC. | .CTGA..AC. | .TTAAG.A-G | .......... | ....CCG.TTA |

FIG. 1A

|  | 205 | 215 | 225 | 235 | 245 |
| --- | --- | --- | --- | --- | --- |
| FLOR | AATAAATCAA | AACTTTCAAC | AACGGATCTC | TTGGTTCTGG | CATCGATGAA |
| DESTA | .......... | .......... | .......... | .......... | .......... |
| DESTB | .......... | .......... | .......... | .......... | .......... |
| DESTC | .......... | .......... | .......... | .......... | .......... |

|  | 255 | 265 | 275 | 285 | 295 |
| --- | --- | --- | --- | --- | --- |
| FLOR | GAACGCAGCG | AAATGCGATA | AGTAATGTGA | ATTGCAGAAT | TCAGTGAATC |
| DESTA | .......... | .......... | .......... | .......... | .......... |
| DESTB | .......... | .......... | .......... | .......... | .......... |
| DESTC | .......... | .......... | .......... | .......... | .......... |

|  | 305 | 315 | 325 | 335 | 345 |
| --- | --- | --- | --- | --- | --- |
| FLOR | ATCGAATCTT | TGAACGCACA | TTGCGCCCGC | CAGTATTCTG | GCGGGCATGC |
| DESTA | .......... | .......... | .......... | C......... | .......... |
| DESTB | .......... | .......... | .......... | C......... | .......... |
| DESTC | .......... | .......... | .......... | T......... | .......... |

|  | 355 | 365 | 375 | 385 | 395 |
| --- | --- | --- | --- | --- | --- |
| FLOR | CTGTTCGAGC | GTCATTTCAA | CCCTCAAGCA | CCTTCGGGAG | CTTGGTGTTG |
| DESTA | .......... | .......... | ........C | C----..G. | .......... |
| DESTB | .......... | .......... | ........C | C----..G. | .......... |
| DESTC | .......... | .......... | ........C | C----..G. | .......... |

FIG. 1B

|  | 405 | 415 | 425 | 435 | 445 |
|---|---|---|---|---|---|
| FLOR | GGGATCGGCA | GGGCGTCCTC | CGGGTCGCGC | OGTCCCCCAA | ATCTAGTGGC |
| DESTA | .A...C.... | ...T.C.CC. | CG.GG.G... | .NS.T..C.. | .....A.... |
| DESTB | .A...N.... | ...T.C.CC. | CG.GG.G... | .NG.T..T.. | .....A.... |
| DESTC | .G...C.... | ...A.C.TC. | -..CG.C... | .GT.C..T.. | .....C.... |

|  | 455 | 465 | 475 | 485 | 495 |
|---|---|---|---|---|---|
| FLOR | GGTCTCGCTG | TAGCTTCCTC | TGCGTAGTAA | TACACCTCGC | TCTGGAGTCT |
| DESTA | .A.C.T.... | .......... | .........G | .C........ | A.....AAAA- |
| DESTB | .A.C.C.... | .......... | .........G | .C........ | A.....AAAA- |
| DESTC | .......... | .......... | .........G | .C........ | A.....GAAA- |

|  | 505 | 515 | 525 | 535 | 545 |
|---|---|---|---|---|---|
| FLOR | CGGTGCGGCC | ACGCCGTAAA | ACCCCCAACT | TTTTTCTGGT | TGACCTCGAA |
| DESTA | .A.C.T.... | ........T. | .......C.. | .C.GAAA.G. | .........G. |
| DESTB | .A.C.C.... | ........T. | .......C.. | .C.GAAA.G. | .........G. |
| DESTC | .A.C.C.... | ........T. | .......A.. | .C.GAAA.T. | .........G. |

|  | 555 | 565 | 575 | 585 | 595 |
|---|---|---|---|---|---|
| FLOR | TCAGGTAGGA | CTACCCGCTG | AACTTAAGCA | TATCAATAAG | CGGAGGA |
| DESTA | .......... | A......... | .......... | .......... | ....... |
| DESTB | .......... | A......... | .......... | .......... | ....... |
| DESTC | .......... | A......... | .......... | .......... | ....... |

DETECTION OF PLANT PATHOGENIC FUNGI

BACKGROUND OF THE INVENTION

FIELD OF THE INVENTION

This invention relates to oligonucleotide probes, which can be used to determine the presence of forest pathogens in nursery seedlings which do not show symptoms.

More specifically, the invention relates to a set of oligonucleotide primers, which when used in a polymerase chain reaction will specifically and preferentially amplify the ribosomal internal transcribed spacer (ITS) of fungi causing forest diseases, namely *Cylindrocarpon floridanum* and *Cylindrocarpon destructans*. The invention also provides a set of probes for the detection and diagnosis of fungi in nursery seedlings.

Root rot is one of the most serious conifer nursery diseases in Canada. *Cylindrocarpon destructans* and *Cylindrocarpon floridanum* are two important causal agents of root rot in nurseries (Saunders et al, Can. J. For. Res. 22:1204-1207 [1992]). While the former is a ubiquitous soil organism (Matturi et al, Trans. Br. Mycol. Soc. 47:577-587 [1964]), the latter is most often found in nurseries and may have been introduced into northern North America. The fungus was first reported in nurseries in Minnesota in 1962 (Anderson et al, Minnesota For. Sci. 8:378-384 [1962]), and in Quebec and Ontario in the late 1960s (Myren et al, Bi-Mon. Re. Notes 31:34 Can. For. Serv.—Ontario [1975]).

The impact of the pathogens on nursery seedlings is two-fold. Firstly, the fungi can cause seedling mortality n nurseries. Up to 50% mortality was reported to be caused by root rots in affected nursery beds (Anderson et al ibid). Secondly, infected seedling have a lower survival rate after outplanting to reforestation sites. Mortality rates of 40% during the first year for black spruce (*Picea mariana*) and 60% two years after outplanting for red pine (*Pinus resinosa*) have been reported (Saunders et al, ibid and Thies et al For. Sci. 17:323-331 [1971]). The problem is compounded by the fact that in some cases the symptoms are not visible on infected seedlings, but disease can develop after transplantation. Seedlings with a healthy appearance had up to 25% root rot induced mortality after transplantation (Saunders et al, ibid).

It is not known whether the pathogens can become established in sites where they were not previously present and if so what damage they can cause. *Cylindrocarpon destructans* has recently been reported to cause root rots on English walnut in Italy (Montecchio et al, Plant Disease 79:967 [1995]). In Quebec, *Cylindrocarpon floridanum* was isolated from the soil in plantations that had been reforested with infected seedlings. Since both fungi have broad host ranges and can infect deciduous trees as well as other annual and perennial plants (Farr et al, Fungi on Plants and Plant Products in the United States, The American Phytopathological Society, St. Paul, Minn. [1989]), it is important to develop the proper tools for monitoring the pathogens following outplanting.

Because of the severe losses reported and the potential for spreading the pathogens, certification programs or grading programs have been put in place in Quebec and Ontario to cull seedlings showing symptoms of disease. In the province of Quebec, 262 million seedlings were inspected in 1993 for certification of health and 4 million seedlings were destroyed because they showed symptoms of root rot. The certification was done by visual inspection followed by random sampling in nursery beds and isolation and identification of organisms present in roots and root collars. In Ontario, 400,000 seedlings were culled in 1986 and 1987 and incidence levels were evaluated between 1 and 40% in individual fields. However, the certification process is time consuming and can lack sensitivity, particularly when aggressive contaminants are present in the roots, preventing isolation of the causal agent (Saunders et al, ibid).

Thus, it is readily apparent that a need exists for the means and a method for detecting plant pathogens directly form infected tissue.

GENERAL DESCRIPTION OF THE INVENTION

The object of the present invention is to meet the above described need by providing oligonucleotide probes specific for *Cylindrocarpon destructans* and *Cylindrocladium floridanum* fungi.

Another object of the invention is to provide an efficient and reliable method of detecting the presence of *Cylindrocarpon destructans* and *Cylindrocarpon floridanum* fungi directly from infected tissue.

Yet another object of the invention is to provide a kit for detecting the present of the species of fungi *Cylindrocarpon destructans* and *Cylindrocarpon floridanum* in infected plant tissue.

According to one aspect, the invention relates to an oligonucleotide probe specific for *Cylindrocarpon destructans* and *Cylindrocarpon floridanum* fungi having a nucleic acid sequence selected from the group consisting of:

| | |
|---|---|
| 5'-TTGTTGCCTCGGCGGTGCCTG-3' | (SEQ ID NO:1) |
| 5'-GGTTTAACGGCGTGGCCGCGCTGTT-3' | (SEQ ID NO:2) |
| 5'-TTCGTTCCCTCGGCGGTGTCCGGCAACG-3' | (SEQ ID NO:3) |
| 5'-CAGGGCGTCCTCCGGGTCGCGCCGT-3' | (SEQ ID NO:4) |

According to another aspect the invention relates to a method of detecting the presence of *Cylindrocarpon destructans* or *Cylindrocarpon floridanum* fungi in a plant tissue sample comprising the steps of:

(a) extracting any fungi DNA from the sample;

(b) hybridizing the DNA with an oligonucleotide probe having a nucleic acid sequence selected from the group consisting of

| | |
|---|---|
| 5'-TTGTTGCCTCGGCGGTGCCTG-3' | (SEQ ID NO:1) |
| 5'-GGTTTAACGGCGTGGCCGCGCTGTT-3' | (SEQ ID NO:2) |
| 5'-TTCGTTCCCTCGGCGGTGTCCGGCAACG-3' | (SEQ ID NO:3) |
| 5'-CAGGGCGTCCTCCGGGTCGCGCCGT-3' | (SEQ ID NO:4); | and (c) detecting the presence of any nucleic acids hybridized with said oligonucleotide indicative of the presence of the fungi.

According to yet another aspect, the invention relates to a method of making an oligonucleotide probe specific to *Cylindrocarpon destructans* and *Cylindrocladium floridanum* fungi comprising the steps of:

(a) amplifying a DNA fragment by a polymerase chain reaction using nucleic acids of said fungi as a template and oligonucleotides having a nucleic acid sequence selected from the group consisting of

5'-TTGTTGCCTCGGCGGTGCCTG-3' (SEQ ID NO:1)

5'-GGTTTAACGGCGTGGCCGCGCTGTT-3' (SEQ ID NO:2)

5'-TTCGTTCCCTCGGCGGTGTCCGGCAACG-3' (SEQ ID NO:3)

5'-CAGGGCGTCCTCCGGGTCGCGCCGT-3' (SEQ ID NO:4);

and as a primer for initiating the reaction;

(b) isolating and purifying the DNA fragment;
(c) sequencing the fragment: and
(d) synthesizing a nucleic acid consisting of a part of said DNA fragment, said part having a nucleic acid sequence which is specific to said species of fungi.

Another aspect of the invention relates to a kit for detecting the present of *Cylindrocarpon destructans* or *Cylindrocarpon floridanum* fungi in a plant tissue comprising primers having the DNA sequences:

5'-TTGTTGCCTCGGCGGTGCCTG-3' (SEQ ID NO:1)

5'-GGTTTAACGGCGTGGCCGCGCTGTT-3' (SEQ ID NO:2)

5'-TTCGTTCCCTCGGCGGTGTCCGGCAACG-3' (SEQ ID NO:3)

5'-CAGGGCGTCCTCCGGGTCGCGCCGT-3' (SEQ ID NO:4)

BRIEF DESCRIPTION OF THE DRAWINGS

Note: In FIG. 1, the sequences are aligned to illustrate the degree of identity between the sequences. A dot indicates the same nucleotide is present as in the top sequence. A dash indicates an insertion/deletion. In the sequence listings which follow, the insertions/deletions represented by the dashes in FIG. 1 have been omitted. This was done in order to simplify a comparison of the sequences in question.

DESCRIPTION OF THE PREFERRED EMBODIMENT

INFECTED MATERIAL

Fungal cultures were made from seedlings collected from several nurseries in Quebec. Between 4 and 16 wood chips approximately 5×10 mm were aseptically excised from roots and root collars of seedling showing symptoms of the disease in order to isolate the two organisms (*C. floridanum* and *C. destructans*), placed on PDA and incubated for 10 days at 20° C. All seedlings from which either *C. floridanum* or *C. destructans* were isolated were subsequently transferred to a freezer at −20° C. until DNA was extracted from the infected root systems.

FUNGAL ISOLATES

Isolates were obtained from infected nursery seedlings belonging to six conifer and one broad-leaved species from eight nurseries and three plantations situated in eight administrative regions in the provide of Quebec (see Table 1).

TABLE 1

Isolates with their host and geographic origin. Samples were isolated from conifer and identified by cultural and morphological means. Presence/absence of species-specific amplicon is indicated by a+ or a− for each set of primers

| Fungal Isolate | Species | Host of Origin | Geographic origin (administrative region)[1] | Species-specific primers[2] | |
|---|---|---|---|---|---|
| | | | | Dest 1-4(ITS variant)[3] | Flor2-5 |
| 1005 | *Cylindrocarpon destructans* | *Picea mariana* | Normandian(02) | +(b) | − |
| 89-0090(1147) | *C. destructans* | *P. glauca* | Duchesnay(03) | +(c) | − |
| 89-0283(1254) | *C. destructans* | *P. mariana* | St-Modeste(01) | +(b) | − |
| 94-1365 | *C. destructans* | *P. abies* | Martinville(05) | +(c) | − |
| 94-0893(1330) | *C. destructans* | *P. rubens* | Berthierville(14) | +(a) | − |
| 94-0001(1331) | *C. destructans* | *Pinus banksiana* | Albanei(02) | +(a) | − |
| 94-1628 | *C. destructans* | *Picea glauca* | St-Prosper(12) | +(a) | − |
| St-Amable | *C. destructans* | *Picea glauca* | St-Amable(06) | +(a) | − |
| 94-0003 | *C. destructans* | *Pinus resinosa* | St-Jean Chrysostome(06) | +(a) | − |
| 94-1685 | *C. destructans* | *P. glauca* | Normandin(02) | +(c) | − |
| Normandin | *C. destructans* | *P. mariana* | Girardville(02) | +(a) | − |
| 92-1382(1073) | *Cylindrocladium floridanium* | *P. mariana* | Duchesnay(03) | − | + |
| 94-1259 | *C. floridanium* | *P. mariana* | Martinville(05) | − | + |
| 92-1482(1070) | *C. floridanium* | *P. mariana* | Normandin(02) | − | + |
| 92-1486(1071) | *C. floridanium* | *P. mariana* | Berthierville(14) | − | + |
| 92-1486(1072) | *C. floridanium* | *P. glauca* | Normandin(02) | − | + |
| Berthler | *C. floridanium* | *P. glauca* | Berthierville(14) | − | + |
| 92-1743(1309) | *C. floridanium* | *P. mariana* | St-Modeste(01) | − | + |
| 92-1708(1258) | *C. floridanium* | *P. mariana* | Ste-Lucas(01) | − | + |
| 94-0893(1329) | *C. floridanium* | *P. rubens* | Berthierville(14) | − | + |
| 94-1913 | *C. floridanium* | *P. mariana* | St-Luce(01) | − | + |
| 94-1383 | *C. floridanium* | *P. glauca* | Grandes-Piles(04) | − | + |
| 93-2023 | *C. floridanium* | *Juglans nigra* | Berthierville(14) | − | + |

TABLE 1-continued

Isolates with their host and geographic origin. Samples were isolated from conifer and identified by cultural and morphological means. Presence/absence of species-specific amplicon is indicated by a+ or a– for each set of primers

| | | | | Species-specific primers[2] | |
|---|---|---|---|---|---|
| Fungal Isolate | Species | Host of Origin | Geographic origin (administrative region)[1] | Dest 1-4(ITS variant)[3] | Flor2-5 |

Figure 1:
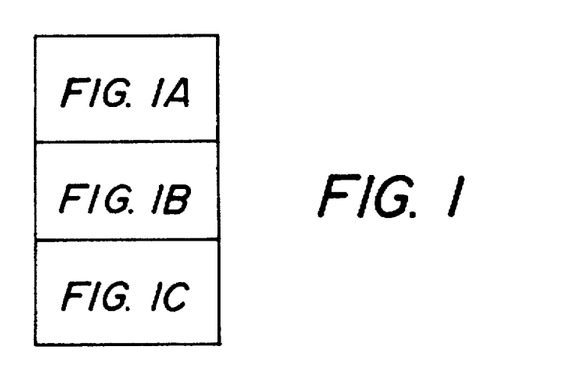
FIGS. 1A, 1B, and 1C are a representation of the sequences of the internal transcribed spacer region, including the 5.8s coding region, of isolates of; *Cylindrocarpon floridanum* and *Cylindrocarpon destructans*(SEQ ID NO: 6, SEQ ID NO: 7 and SEQ ID NO: 8)
Figure 1A:
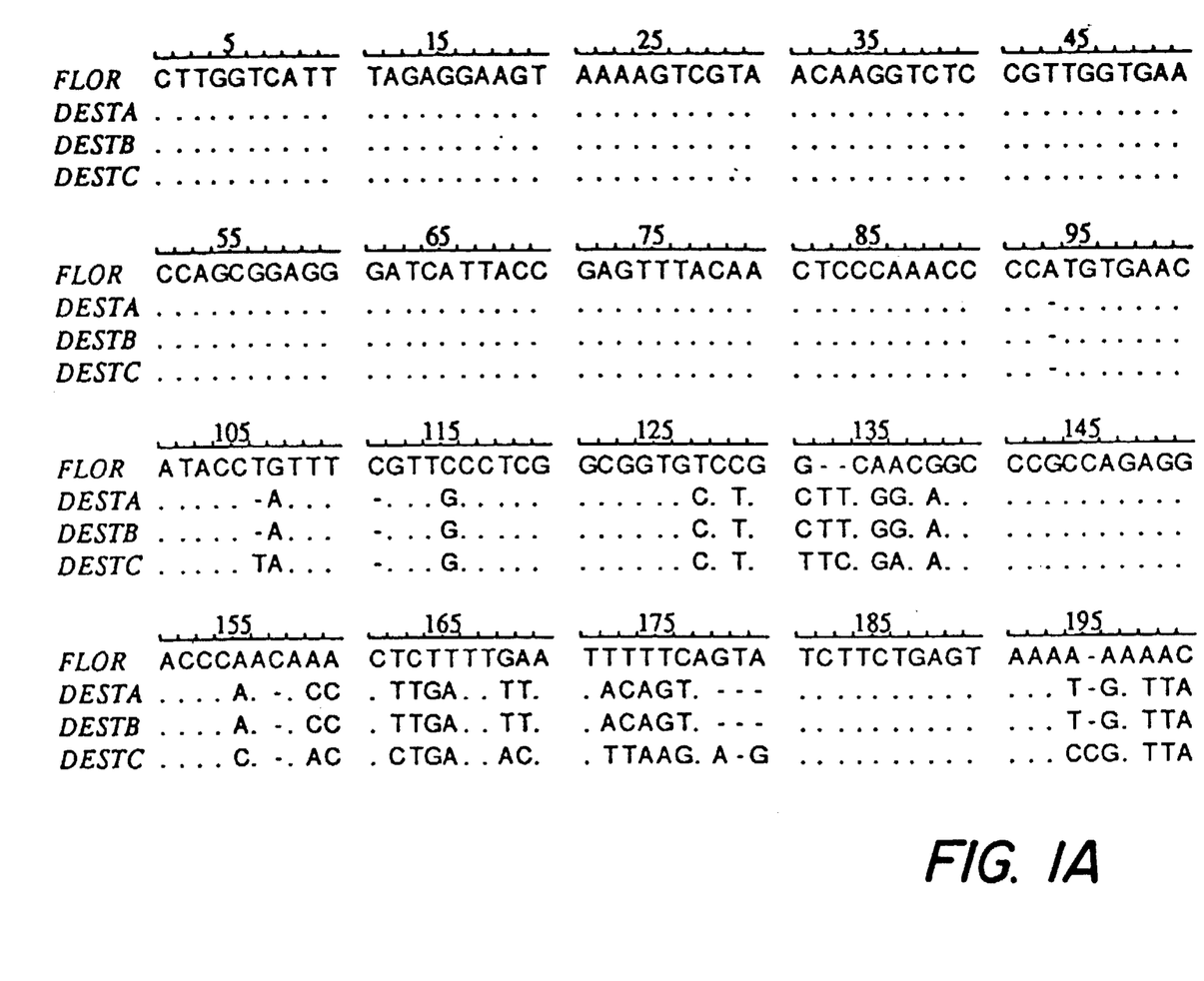
Figure 1B:
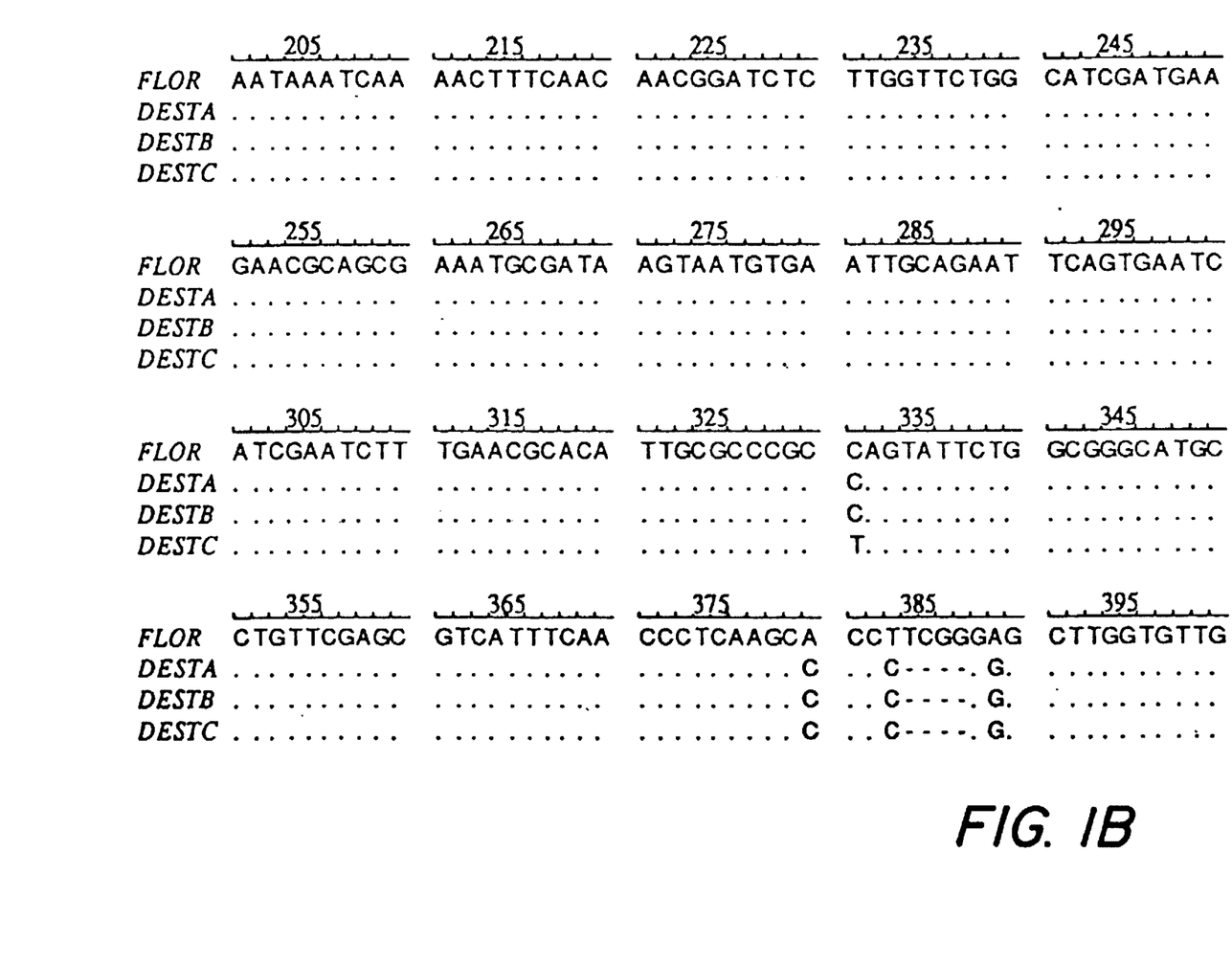
Figure 1C:
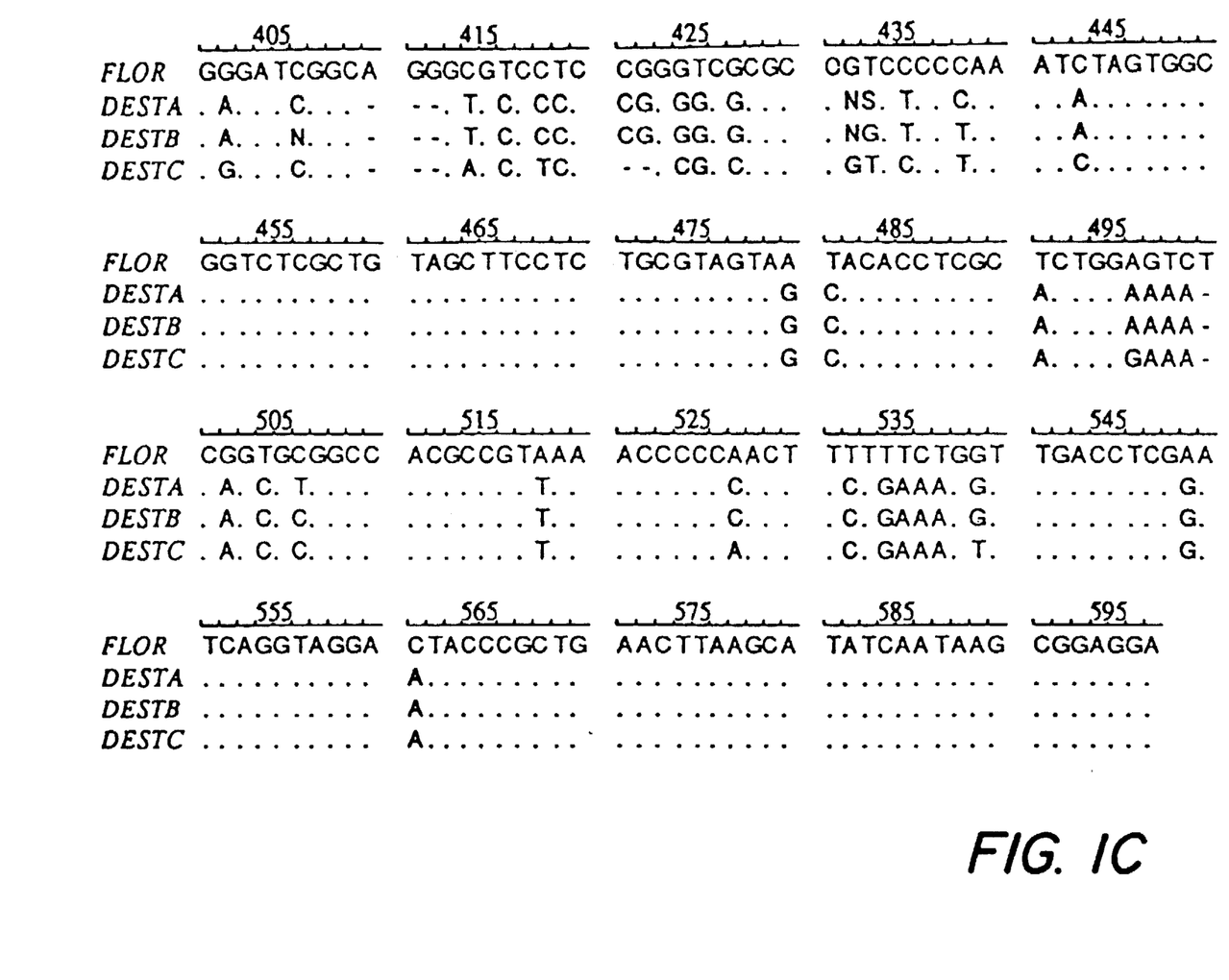

[1]Administrative regions(2)
[2]Primer sequences are given in Table 2
[3]The three ITS variants with *C. destructans* are described in FIG. 1

Additional isolates were obtained form the fungal collection of the Quebec Ministry of Natural Resources. Cultures belonging to the genus Cylindrocladium were transferred to PDA dishes and exposed to light until the formation of vesicles to confirm the species (as per Crous et al, Mycotaxon 84:497–904 [1992] and Crous et al, Mycotaxon LI:341–435 [1994]). Cultures identified as *Cylindrocarpon spp.* were transferred to synthetic nutrient agar (SNA) petri dishes, cultured for a month and monitored for the formation of chlamydospores. Isolates were classified to species according to their morphological, cultural, and sporulation characteristics (see Booth, Mycological papers 104:1–56. Commonwealth Center of Mycology [1966], Domsh et al, Compendium of soil fungi, Academic Press, London [1980] and Samuels et al, Mycol. Res. 94:433–442 [1990]).

Eleven isolates of *C. destructans* and twelve of *C. floridanum* that clearly satisfied the species criteria were included for sequencing and as positive controls for the species-specific primers. These isolates were grown in a liquid broth at 20° C. for 10 days. The mycelium was then filtered through filter paper (Whatman#1) and rinsed with sterile distilled water, lyophilized, and stored at –20° C. until DNA extraction. Isolates from 26 contaminants commonly encountered when isolating fungi from roots were cultured and processed for DNA extraction, as described for root rot organisms. These included *Botrytis cinerea, Sirococcus conigenus, Pestalotiopsis funerea, Gliocladium roseum, Mycelium radicis atrovirens*, isolates belonging to *Fusarium spp.*(9), *Phomopsis spp.*(1), *Coniothyrium spp.*(1). In additional to unidentified hyphomycetes (3), coelomycetes (3), deuteromycete (1), and three non-sporulating basidiomycetes. In additional, isolates identified as *Cylindrocarpon spp.* other than destructans were tested.

DNA EXTRACTION

DNA was extracted according to a modification of a protocol described elsewhere (see Zolan et al, Mol. Cell. Biol. 5:195–200 [1986]). Approximately 10 mg of lyophilized mycelium was mixed with 20 mg of diatomaceous earth and ground in 700 μl of extraction buffer (700 mM NaCl, 50 mM Tri-HCl [pH8], 10 mM EDTA, 1% b-2-mercaptoethanol, 1% cetyl-trimethyl-ammonium bromide). The mixture was incubated at 65° C. for 1h and extracted by adding an equal volume of chloroform-isoamyl alcohol (24:1), vortexing, and centrifuging for 5 min at 10,000×g. The aqueous phase was precipitated with cold isopropanol and centrifuged for 5 min at 10,000×g. The pellets were washed with 70% ethanol, air dried, resuspended in 50 μl of TE8 (10 mM Tris-HCl [pH 8 ], 1 mM EDTA), and stored at –20° C. until needed.

For DNA extractions directly from root collars, the outer bark of the collar was removed with a scalpel and two to four strips of wood (approx. 3×20 mm) were excised and ground in 400 μl of Qiagen extraction buffer (100 mM Tris-HCl, [pH 9.5], 2% CTAB, 1.4 M NaCl 1% PEG 8000, 20 mM EDTA, 1% β-mercapto-ethanol) mixed with approximately 10 mg of diatomaceous earth. Extracts were vortexed, incubated at 65° C. for approximately 1 hr, extracted once with 400 μl of phenol:chloroform: isoamyl alcohol (25:24:1), and centrifuged at 10,000×g for 5 min. The supernatant was transferred to a new microtube, precipitated with one volume of isopropanol, and centrifuged at 10,000×g for 5 min. Pellets were washed with 70% ethanol, air-dried overnight and resuspended in 20 μl TE buffer (pH 8). For DNA extractions from roots, entire rootlets were cut into small pieces and processed as above.

DNA AMPLIFICATIONS, PURIFICATION AND SEQUENCING

The entire region containing portions of the small subunit (18s) both internal transcribed spacers (ITS) and the 5.8s of the rDNA repeat unit was amplified with oligonucleotide ITSIF (fungus-specific:

5'-CTTGGTCATTTAGAGGAAGTAA-3'    (SEQ ID NO:9)

see Gardes et al, Mol. Ecol. 2:113–118 [1993]) and ITS4 (universal:

5'-TCCTCCGCTTATTGATATGC-3'    (SEQ ID NO.:10)

see White et al,
  Amplification and Direct Sequencing of Fungal Ribosomal RNA Genes for Phylogenetics, p.315–322. In M. Innis (ed), PCR protocols: A guide to Methods and Applications. Academic Press, San Diego [1990]). PCR reactions were carried out in volumes of 25 μl containing 10 mM Tris-HCL (pH 8.3) 50 mM KCL, 1.5 mM $MgCl_2$, 0.0001% gelatin, 400 μM dNTPs, 1 μM of each of ITSIF and ITS4 primers, 1 unit of TAQ DNA polymerase (Boehringer Mannhein Biochemica, Mannheim, Germany), and 1 μl of template DNA. The reactions were carried out on an MJ-Research PTC-60 thermal cycler (Watertown, Mass.) and consisted of an initial denaturation of 95° C. for 3 min followed by 30 cycles of 92° C. for 30 s, 55° C. for 30 s and 72° C. for 1 min. The reaction was completed by a 10 min extension at 72° C.

PCR products were purified on a minispin column (Wizard Kit, Promega, Wis.) and sequenced with a DNA Direct Sequencing kit (Gibco-BRL, Md.) according to the manufacturer's recommendations with γp[33] ATP (Amersham, Ill.) labelling of the primers.

PRIMER SYNTHESIS AND TWO-STEP NESTED PCR

Following sequence alignment (GCG software package) with related fungi in Genbank, primers were synthesized on a Beckman synthesizer according to the manufacturer's recommendations. In order to conduct multiplex PCR, primers were designed to amplify PCR products of different lengths for the two target species. Specificity of the Dest1 5'-TTGTTGCCTCGGCGGTGCCTG-3'(SEQ ID NO:1) and Dest4 5'-GGTTTAACGGCGTGGCCGCGCTGTT-3'(SEQ ID NO:2) for *C. destructans* and Flor2 5'-TTCGTTCCCTCGGCGGTGTCCGGCAACG-3'(SEQ ID NO:3) and Flor5 5'-CAGGGCGTCCTCCGGGTCGCGCCGT-3'(SEQ ID NO:4) for *C. floridanum* was tested on all *C. floridanum* and *C. destructans* DNA templates, as well as with DNA templates of the 26 common contaminants.

A nested primer PCR combined with a multiplex PCR approach was used for detection of infected tissues (as per Hensen, Mycol. Res. 96:629–636 [1992] and Hensen et al. Phytopathology 83:283–287 [1993]). Fungi present in roots and root collars of 34 infected seedlings and 2 healthy seedlings were identified by isolation as described above. The DNA was extracted from the root collars and diluted 1:100; and 1 μl was pipetted in a PCR reaction using ITSIF and ITS4 primers to amplify the entire ITS region using the amplification profile described above. A second amplification with all four species-specific internal primers was conducted using as a template 1 μl of PCR product from the previous fungus-specific amplification. Only 15 cycles were run with denaturation at 94° C. to increase specificity. Positive (genomic DNA from the target fungus) and negative (no template DNA) controls were included in all tests.

PCR products were separated by gel electrophoresis on agarose in TAE buffer or on 1% agarose and 1% Synergel (Certified Biotech) in TPE buffer and visualized by UV fluorescence.

RESULTS

All isolates of *C. floridanum* had the same ITS sequence. However, as shown in FIG. 1 some intra-specific variability was found in the ITS sequences within the collection of *C. destructans*. Three groups were identified within *C. destructans* based on their ITS sequences. One group, Dest C, was clearly more divergent from Dest A and Dest B. As also shown in FIG. 1, there were 4 insertion/deletions (indel), 16 transitions, and 12 transversions between Dest A and B, and Dest C. There were no indels and only one transition and one transversion between Dest A and Dest B. There was also some variability within the groups; for example, there was a transversion within Dest A at position 433 and two insertions within Dest C at positions 435 (T) and 537 (A) (results not shown).

All *C. destructans* isolates were formally identified as belonging to this species according to the following morphological and cultural characteristics; 1-chlamydospores were produced in the mycelium and sometimes in the macroconidia; 2-micro-conidia (6–11×2–4 μm) zero to one-septate were present; 3-macro-conidia were 1–3 [4] septate, straight, cylindrical with a round apical cell, and 4-the cultures were pigmented brown to dark brown.

Species-specific primers were selected in regions that were variable between, but fairly conserved within, species. Primers Flor2 5'-TTCGTTCCCTCGGCGGTGTCCGGCAACG-3' (SEQ ID NO:3) and Flor5 5'-CAGGGCGTCCTCCGGGTCGCGCCGT-3'(SEQ ID NO:4) were designed to amplify a 328 bp PCR product starting at position 109 in *C. floridanum* (FIG. 1 and Table 2 below). Two primers were designed to amplify a 400 bp amplicon in variants Dest A and Dest B and a 299 bp amplicon in Dest C of *C. destructans* (FIG. 1 and Table 2 below). The mismatch at the priming site in Dest C was situated in the center of the primer Dest 4: at the annealing temperature used in our study, amplification of a product in Dest C was not prevented by this mismatch (Table 2).

TABLE 2

List of primers used for specific amplification of *Cylindrocarpon destructans* and *Cylindrocladium floridanum*

| Primer name* | Primer Sequence |
|---|---|
| Dest1 | 5'-TTGTTGCCTCGGCGGTGCCTG-3' |
| Dest4 | 5'-GGTTTAACGGCGTGGCCGCGCTGTT-3' |
| Flor2 | 5'-TTCGTTCCCTCGGCGGTGTCCGGCAACG-3' |
| Flor5 | 5'-CAGGGCGTCCTCCGGGTCGCGCCGT-3' |

*Primers Flor2 and Flor5 when used in combination amplify a 328 bp fragment in *C. floridanum* primers; and Dest1 and Dest4 amplify a 400 bp product in *C. destructans* variant Dest A and Dest B and a 399 bp product in variant Dest C.

Figure 2:
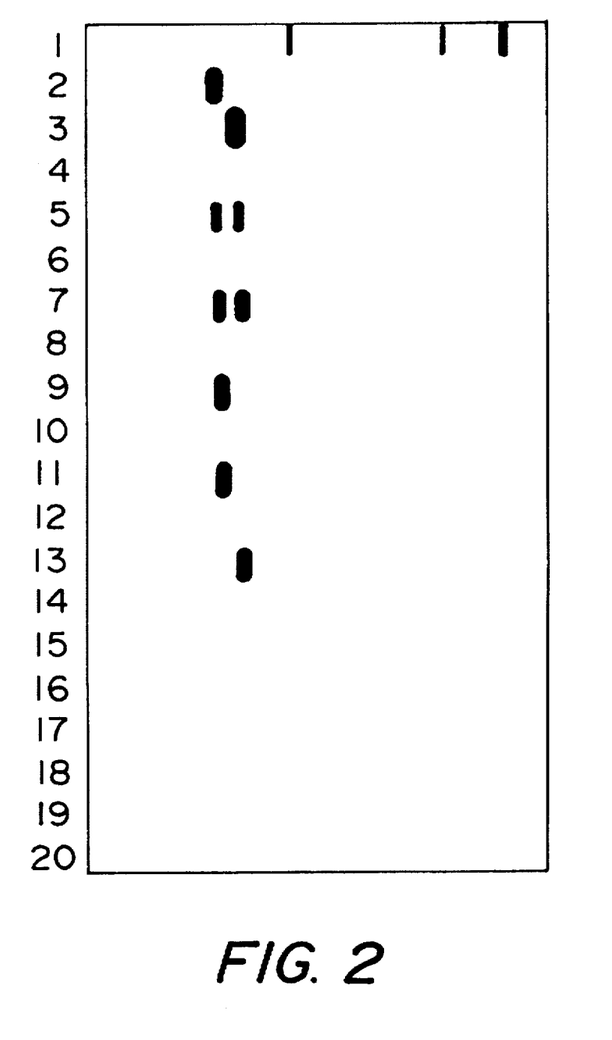
FIG. 2 is a representation of an electrophorgram of amplification of the internal transcribed spacer of root rot fungi and associated fungi.

Specificity of the primers was confirmed on genomic DNA from all cultures of *C. floridanum* and *C. destructans*. As shown in FIG. 2, no amplification resulted from PCR reactions using either set of primers with contaminant genomic DNA as template, including closely related species of Cylindrocarpon.

In FIG. 2, lane 1 represents Pharmacia's 100 bp ladder, lane 2 represents *C. floridanum* positive control (1070), lane 3 represents *C. destructans* positive control, lanes 4–11 represent root-collar and lanes 12 and 13 rootlet DNA extracts, lanes 14–17 represent DNA extracts from healthy seedlings, and lanes 18 to 20 represent Fusarium spp. Gliocladiumroseum and Botrytiscinerea, respectively. Lanes 4, 6, 8, 10, 12, 14 and 15 were amplified with ITSIF and ITS4; lanes 5, 7, 9, 11, 13, 16 and 17 represent round amplification with the primers Flor 2, Flor5, Dest1 and Dest4 using amplification products from ITSF-ITS4 (lanes 4, 6, 8, 10, 12, 14 and 15) as a template. *Cylindrocarpon floridanum* and *Cylindrocarpon destructans* were isolated from seedlings in lanes 4–7. Only *C. floridanum* was isolated form seedlings in lanes 8–11, and only *C. destructans* was isolated from seedlings in lanes 12–13.

The first round of amplification from infected tissues using primers ITSIF and ITS4 resulted in PCR products of variable sizes, as would be expected if several funga species were associated with decaying roots (FIG. 2). However, the second round of amplification with all four specific primers in a multiplex PCR reaction yielded either one or two amplicons of the expected size (FIG. 2). Referring to Table 3, *Cylindrocarpon floridanum* was detected in 31/34 infected seedlings form which it was isolated. In two cases, the fungus was detected in the seedlings by PCR but was not isolated. In the two healthy seedlings, the fungus was not isolated and the diagnostic PCR was negative. *Cylindrocarpon destructans* was detected in 19/30 infected seedlings from which the fungus was isolated and three seedlings from which only *C. floridanum* was isolated. On eight of the infected seedlings, the diagnostic PCR on DNA extracts from root collars was negative for *C. destructans* but the fungus was isolated from rootlets. The multiplex PCR was effective as the two expected products were amplified simultaneously in 20 reactions (FIG. 2).

TABLE 3

Root rot fungi isolated from the roots and root collars of nursery seedlings and the results of amplification with two-step nested PCR using species-specific primers.

| Fungal species | PCR +/ isolation + | PCR +/ isolation − | PCR −/ isolation + | PCR −isolation −[a] |
|---|---|---|---|---|
| C. floridanum | 31 | 2 | 1 | 2 |
| C. destructans | 19 | 3 | 8b | 6 |

[a]Including two healthy control seedlings
[b]C. destructans was isolated from rootlets, but was not amplified from the root collars was not very efficient, probably due to desiccation during storage (see discussion).

DISCUSSION

Thus, there has been illustrated the detection of root rot fungi directly from infected seedlings with a minimum of manipulation. This approach is particularly well suited to soil organisms that are difficult to identify or isolate due to the presence of other aggressive species.

It was possible to extract large quantities of DNA from the root collars of both infected and healthy seedlings. However, DNA extraction and amplification from rootlets was not very efficient. Such rootlets may have been dead for some time before the seedlings were harvested or they might have been more susceptible than root collars to desiccation in storage. Several different extraction protocols were compared, and it was found that the one described herein was the most reliable. Some of the extraction buffers based on SDS or CTAB yielded DNA extracts that contained high levels of inhibitors; diluting these extracts 1:1000 and adding 1 µl to a PCR reaction already containing genomic DNA of the target fungus completely prevented amplification of the expected PCR product (results not shown).

Some of the DNA samples were extracted from seedlings that had been in storage at −20° C. for one year. This has important implications for detection on an operational basis since large numbers of samples could be frozen during the fall inspection and processed during the winter before outplanting in the spring.

Amplification of species-specific PCR products directly from DNA extracts from the roots without a first round of fungus-specific amplification was not very consistent, probably due to the variability in the ratio of target DNA to non-target DNA. Multiplex PCR with all four primers directly from infected roots without a first round of amplifications was extremely unreliable.

Amplification of the species-specific PCR fragments with individual primer combinations (Flor2 and Flor5, Dest1 and Dest4) from genomic DNA was generally more successful than multiplex PCR using all four primers. When a mixture of genomic DNA from the two fungi was used as a template with all four primers, competition between the two amplicons appeared to cause inconsistent results, i.e. often only one PCR product was amplified even though genomic DNA from the two fungi was used as a template. Similar results were reported for multiplex PCR in other organisms (Bourque et al. Appln. Environ. Microbiol., 59:523–527 [1993].

By contrast, the nested multiplex PCR approach presented here yielded highly consistent and reproducible results. The first amplification with fungus-specific primers preferentially increased the population of fungal ITS molecules, thereby increasing the ratio of fungal:host ITS molecules. Competition between the two PCR products was apparently reduced during the second round of amplification since large numbers of ITS molecules served as a template to the species-specific primers.

Detection with the PCR assay was mostly concordant with results from the isolation procedure. With one exception, all seedlings infected by C. floridanum tested positive with the PCR assay. This is important because this fungus is believed to be the primary root rot pathogen in conifer nurseries in northeastern North America. In addition, this fungus was detected in seedlings from which the fungus had not been isolated. This can be explained by the fact that isolations are not always successful, in particular if aggressive contaminants are also present on the roots. Alternatively, infected seedlings with dead mycelium might test positive even though the fungus cannot be isolated, since DNA can be amplified from dead mycelium.

The fungus was frequently detected by PCR in seedlings where C. destructans was not isolated in the root collars but was isolated in rootlets (Table 3). This could be an indication that the pathogen was present in the root collars at some point during the etiology, but receded to the roots subsequently. This fungus was found to survive on infected roots of cultivated strawberry for 15 weeks after which it was replaced by other saprophytes (Matturi et al. supra). Since C. destructans is believed to be either a seek pathogen, or a secondary parasite, it may be less important to detect than C. floridanum.

I claim:

1. An oligonucleotide probe specific for *Cylindrocarpon destructans* and *Cylindrocarpon floridanum* fungi having a nucleic acid sequence selected from the group consisting of:

5'-TTGTTGCCTCGGCGGTGCCTG-3' (SEQ ID NO:1)

5'-GGTTTAACGGCGTGGCCGCGCTGTT-3' (SEQ ID NO:2)

5'-TTCGTTCCCTCGGCGGTGTCCGGCAACG-3'(SEQ ID NO:3)

and

5'-CAGGGCGTCCTCCGGGTCGCGCCGT-3' (SEQ ID NO:4).

2. A method of detecting the presence of *Cylindrocarpon destructans* or *Cylindrocarpon floridanum* fungi in a plant tissue sample comprising the steps of:

(a) extracting any fungi DNA from the sample;

(b) contacting the DNA with an oligonucleotide probe having a nucleic acid sequence selected from the group consisting of         5'-TTGTTGCCTCGGCGGTGCCTG-3' (SEQ ID NO:1)

5'-GGTTTAACGGCGTGGCCGCGCTGTT-3' (SEQ ID NO:2)

5'-TTCGTTCCCTCGGCGGTGTCCGGCAACG-3'(SEQ ID NO:3)

and

5'-CAGGGCGTCCTCCGGGTCGCGCCGT-3' (SEQ ID NO:4);

and

(c) detecting the presence of any nucleic acids hybridized with said oligonucleotide indicative of the presence of the fungi.

3. A method of making an oligonucleotide probe specific to *Cylindrocarpon destructans* and *Cylindrocladium floridanum* fungi comprising the steps of:

(a) amplifying a DNA fragment by a polymerase chain reaction using nucleic acids of said fungi as a template and an oligonucleotide having a nucleic acid sequence selected from the group consisting of         5'-TTGTTGCCTCGGCGGTGCCTG-3' (SEQ ID NO:1)

5'-GGTTTAACGGCGTGGCCGCGCTGTT-3' (SEQ ID NO:2)

5'-TTCGTTCCCTCGGCGGTGTCCGGCAACG-3'(SEQ ID NO:3)

and

5'-CAGGGCGTCCTCCGGGTCGCGCCGT-3' (SEQ ID NO:4);

as a primer for initiating the reaction;

(b) isolating and purifying the DNA fragment;

(c) sequencing the fragment: and (d) synthesizing a nucleic acid consisting of said DNA fragment, having a nucleic acid sequence which is specific to said species of fungi.

4. A kit for detecting the presence of *Cylindrocarpon destructans* or *Cylindrocarpon floridanum* fungi in a plant tissue comprising primers having the DNA sequences:

5'-TTGTTGCCTCGGCGGTGCCTG-3'   (SEQ ID NO:1)

5'-GGTTTAACGGCGTGGCCGCGCTGTT-3   '(SEQ ID NO:2)

5'-TTCGTTCCCTCGGCGGTGTCCGGCAACG-3'(SEQ ID NO:3)

and

5'-CAGGGCGTCCTCCGGGTCGCGCCGT-3'   (SEQ ID NO:4).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:1:

TTGTTGCCTC GGCGGTGCCT G    21

( 2 ) INFORMATION FOR SEQ ID NO:2:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i x ) SEQUENCE DESCRIPTION: SEQ ID NO:2:

| GGTTTAACGG | CGTGGCCGCG | CTGTT | | | 25 |

( 2 ) INFORMATION FOR SEQ ID NO:3:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i x ) SEQUENCE DESCRIPTION: SEQ ID NO:3:

| TTCGTTCCCT | CGGCGGTGTC | CGGCAACG | | | 28 |

( 2 ) INFORMATION FOR SEQ ID NO:4:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i x ) SEQUENCE DESCRIPTION: SEQ ID NO:4:

| CAGGGCGTCC | TCCGGGTCGC | GCCGT | | | 25 |

( 2 ) INFORMATION FOR SEQ ID NO:5:

( i ) SEQUENCE CHARACTERISTICS:
  ( A ) LENGTH: 594
  ( B ) TYPE: nucleic acid
  ( C ) STRANDEDNESS: double
  ( D ) TOPOLOGY: linear ( i x ) SEQUENCE DESCRIPTION: SEQ ID NO:5:

| CTTGGTCATT | TAGAGGAAGT | AAAAGTCGTA | ACAAGGTCTC | CGTTGGTGAA | 50 |
| CCAGCGGAGG | GATCATTACC | GAGTTTACAA | CTCCCAAACC | CCATGTGAAC | 100 |
| ATACCTGTTT | CGTTCCCTCG | GCGGTGTCCG | GCAACGGCCC | GCCAGAGGAC | 150 |
| CCAACAAACT | CTTTTGAATT | TTTCAGTATC | TTCTGAGTAA | AAAAAACAAT | 200 |
| AAATCAAAAC | TTTCAACAAC | GGATCTCTTG | GTTCTGGCAT | CGATGAAGAA | 250 |
| CGCAGCGAAA | TGCGATAAGT | AATGTGAATT | GCAGAATTCA | GTGAATCATC | 300 |
| GAATCTTTGA | ACGCACATTG | CGCCCGCCAG | TATTCTGGCG | GGCATGCCTG | 350 |
| TTCGAGCGTC | ATTTCAACCC | TCAAGCACCT | TCGGGAGCTT | GGTGTTGGGG | 400 |
| ATCGGCAGGG | CGTCCTCCGG | GTCGCGCCGT | CCCCCAAATC | TAGTGGCGGT | 450 |
| CTCGCTGTAG | CTTCCTCTGC | GTAGTAATAC | ACCTCGCTCT | GGAGTCTCGG | 500 |
| TGCGGCCACG | CCGTAAAACC | CCCAACTTTT | TTCTGGTTGA | CCTCGAATCA | 550 |
| GGTAGGACTA | CCCGCTGAAC | TTAAGCATAT | CAATAAGCGG | AGGA | 594 |

( 2 ) INFORMATION FOR SEQ ID NO:6:

( i ) SEQUENCE CHARACTERISTICS:
  ( A ) LENGTH: 581
  ( B ) TYPE: nucleic acid
  ( C ) STRANDEDNESS: double
  ( D ) TOPOLOGY: linear ( i x ) SEQUENCE DESCRIPTION: SEQ ID NO:6:

| | | | | | |
|---|---|---|---|---|---|
| CTTGGTCATT | TAGAGGAAGT | AAAAGTCGTA | ACAAGGTCTC | CGTTGGTGAA | 50 |
| CCAGCGGAGG | GATCATTACC | GAGTTTACAA | CTCCCAAACC | CCTGTGAACA | 100 |
| TACCATTTGT | TGCCTCGGCG | GTGCCTGCTT | CGGCAGCCCG | CCAGAGGACC | 150 |
| CAAACCCTTG | ATTTTATACA | GTATCTTCTG | AGTAAATGAT | TAAATAAATC | 200 |
| AAAACTTTCA | ACAACGGATC | TCTTGGTTCT | GGCATCGATG | AAGAACGCAG | 250 |
| CGAAATGCGA | TAAGTAATGT | GAATTGCAGA | ATTCAGTGAA | TCATCGAATC | 300 |
| TTTGAACGCA | CATTGCGCCC | GCCAGTATTC | TGGCGGGCAT | GCCTGTTCGA | 350 |
| GCGTCATTTC | AACCCTCAAG | CCCCCGGGCT | TGGTGTTGGA | GATCGGCGTG | 400 |
| CCCCCCGGGG | CGCGCCNSCT | CCCAAATATA | GTGGCGGTCT | CGCTGTAGCT | 450 |
| TCCTCTGCGT | AGTAGCACAC | CTCGCACTGG | AAAACAGCGT | GGCCACGCCG | 500 |
| TTAAACCCCC | CACTTCTGAA | AGGTTGACCT | CGGATCAGGT | AGGAATACCC | 550 |
| GCTGAACTTA | AGCATATCAA | TAAGCGGAGG | A | | 581 |

( 2 ) INFORMATION FOR SEQ ID NO:7:

( i ) SEQUENCE CHARACTERISTICS:
( A ) LENGTH: 531
( B ) TYPE: nucleic acid
( C ) STRANDEDNESS: double
( D ) TOPOLOGY: linear ( i x ) SEQUENCE DESCRIPTION: SEQ ID NO:7:

| | | | | | |
|---|---|---|---|---|---|
| CCAGCGGAGG | GATCATTACC | GAGTTTACAA | CTCCCAAACC | CCTGTGAACA | 50 |
| TACCATTTGT | TGCCTCGGCG | GTGCCTGCTT | CGGCAGCCCG | CCAGAGGACC | 100 |
| CAAACCCTTG | ATTTTATACA | GTATCTTCTG | AGTAAATGAT | TAAATAAATC | 150 |
| AAAACTTTCA | ACAACGGATC | TCTTGGTTCT | GGCATCGATG | AAGAACGCAG | 200 |
| CGAAATGCGA | TAAGTAATGT | GAATTGCAGA | ATTCAGTGAA | TCATCGAATC | 250 |
| TTTGAACGCA | CATTGCGCCC | GCCAGTATTC | TGGCGGGCAT | GCCTGTTCGA | 300 |
| GCGTCATTTC | AACCCTCAAG | CCCCCGGGCT | TGGTGTTGGA | GATNGGCGTG | 350 |
| CCCCCCGGGG | CGCGCCNGCT | CCTAAATATA | GTGGCGGTCT | CGCTGTAGCT | 400 |
| TCCTCTGCGT | AGTAGCACAC | CTCGCACTGG | AAAACAGCGC | GGCCACGCCG | 450 |
| TTAAACCCCC | CACTTCTGAA | AGGTTGACCT | CGGATCAGGT | AGGAATACCC | 500 |
| GCTGAACTTA | AGCATATCAA | TAAGCGGAGG | A | | 531 |

( 2 ) INFORMATION FOR SEQ ID NO:8:

( i ) SEQUENCE CHARACTERISTICS:
( A ) LENGTH: 583
( B ) TYPE: nucleic acid
( C ) STRANDEDNESS: double
( D ) TOPOLOGY: linear ( i x ) SEQUENCE DESCRIPTION: SEQ ID NO:8:

| | | | | | |
|---|---|---|---|---|---|
| CTTGGTCATT | TAGAGGAAGT | AAAAGTCGTA | ACAAGGTCTC | CGTTGGTGAA | 50 |
| CCAGCGGAGG | GATCATTACC | GAGTTTACAA | CTCCCAAACC | CCTGTGAACA | 100 |
| TACCTATTTG | TTGCCTCGGC | GGTGCCTGTT | CCGACAGCCC | GCCAGAGGAC | 150 |
| CCCAAACCCT | GATTACATTT | AAGAAGTCTT | CTGAGTAAAC | CGATTAAATA | 200 |
| AATCAAAACT | TTCAACAACG | GATCTCTTGG | TTCTGGCATC | GATGAAGAAC | 250 |

-continued

```
GCAGCGAAAT  GCGATAAGTA  ATGTGAATTG  CAGAATTCAG  TGAATCATCG          300

AATCTTTGAA  CGCACATTGC  GCCCGCTAGT  ATTCTGGCGG  GCATGCCTGT          350

TCGAGCGTCA  TTTCAACCCT  CAAGCCCCCG  GGCTTGGTGT  TGGGGATCGG          400

CGAGCCTCCG  CGCCCGCCGT  CCCCTAAATC  TAGTGGCGGT  CTCGCTGTAG          450

CTTCCTCTGC  GTAGTAGCAC  ACCTCGCACT  GGGAAACAGC  GCGGCCACGC          500

CGTTAAACCC  CCAACTTCTG  AAAGTTTGAC  CTCGGATCAG  GTAGGAATAC          550

CCGCTGAACT  TAAGCATATC  AATAAGCGGA  GGA                             583
```

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:9:

```
CTTGGTCATT  TAGAGGAAGT  AA                                           22
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:10:

```
TCCTCCGCTT  ATTGATATGC                                               20
```